United States Patent [19]

Ginocchio

[11] 4,237,591
[45] Dec. 9, 1980

[54] DEODORANT MINI-PAD SANITARY NAPKIN

[75] Inventor: James A. Ginocchio, Summit, N.J.

[73] Assignee: Personal Products Company, Milltown, N.J.

[21] Appl. No.: 9,217

[22] Filed: Feb. 5, 1979

Related U.S. Application Data

[62] Division of Ser. No. 799,850, May 23, 1977, abandoned.

[51] Int. Cl.³ .......................... D06B 3/02; D04H 5/08
[52] U.S. Cl. ..................................... 28/121; 118/308;
128/290 P; 128/296; 264/121; 264/134;
264/136; 264/174; 427/180; 427/206;
427/434.2; 427/434.6
[58] Field of Search .................. 427/434 D, 177, 377,
427/180, 434.2, 434.6; 128/284, 285, 290 R, 290
W, 290 P, 296, 295; 264/121, 134, 136, 174, 257;
19/299, 304, 145, 150; 424/28; 28/118, 120,
121; 156/62.2, 62.4

[56] References Cited

U.S. PATENT DOCUMENTS

| 1,670,587 | 5/1928 | Mahler | 427/177 |
|---|---|---|---|
| 1,729,752 | 10/1929 | Southgate | 128/290 R |
| 1,767,209 | 6/1930 | Gladding | 427/177 |
| 1,932,383 | 10/1933 | Richardson | 128/285 |
| 2,024,145 | 12/1935 | Cline | 128/290 R |
| 2,067,961 | 1/1937 | Williams | 128/296 |
| 2,086,757 | 7/1937 | Williams | 156/62.2 |
| 2,217,049 | 10/1940 | Greenleaf | 19/145 |
| 2,411,326 | 11/1946 | McMillin et al. | 156/62.4 |
| 2,542,909 | 2/1951 | Dewet | 128/290 R |
| 2,543,101 | 2/1951 | Francis | 19/145 |
| 2,690,415 | 9/1954 | Shuller | 128/290 R |
| 2,704,734 | 3/1955 | Draper et al. | 156/62.4 |
| 2,943,010 | 6/1960 | Stefl et al. | 19/145 |
| 3,344,789 | 10/1967 | Arnold et al. | 128/295 |
| 3,347,237 | 10/1967 | Jones | 128/285 |
| 3,420,234 | 1/1969 | Phelps | 128/285 |
| 3,587,579 | 6/1971 | Sabee | 128/287 |
| 3,691,271 | 9/1972 | Charle et al. | 128/285 |
| 3,800,797 | 4/1974 | Tune | 128/290 R |
| 3,815,600 | 6/1974 | Roves | 128/285 |
| 3,856,012 | 12/1974 | MacDonald et al. | 128/284 |
| 3,856,014 | 12/1974 | Yamauchi | 128/290 R |
| 3,862,867 | 1/1975 | Marshall | 156/62.2 |
| 4,019,517 | 4/1977 | Glassman | 128/284 |

FOREIGN PATENT DOCUMENTS

| 117704 | 11/1943 | Australia | 128/290 W |
| 1003597 | 9/1965 | United Kingdom | 427/180 |

Primary Examiner—W. E. Hoag
Attorney, Agent, or Firm—Jason Lipow

[57] ABSTRACT

A sanitary napkin is provided containing a perfume composition and means for inhibiting migration of components of the perfume composition. Means comprise providing within the napkin at least one elongated narrow strip element. The strip element carries the perfume composition and extends generally longitudinally within the napkin. Preferably, the strip element is a cellulosic string.

8 Claims, 6 Drawing Figures

U.S. Patent
Dec. 9, 1980
4,237,591
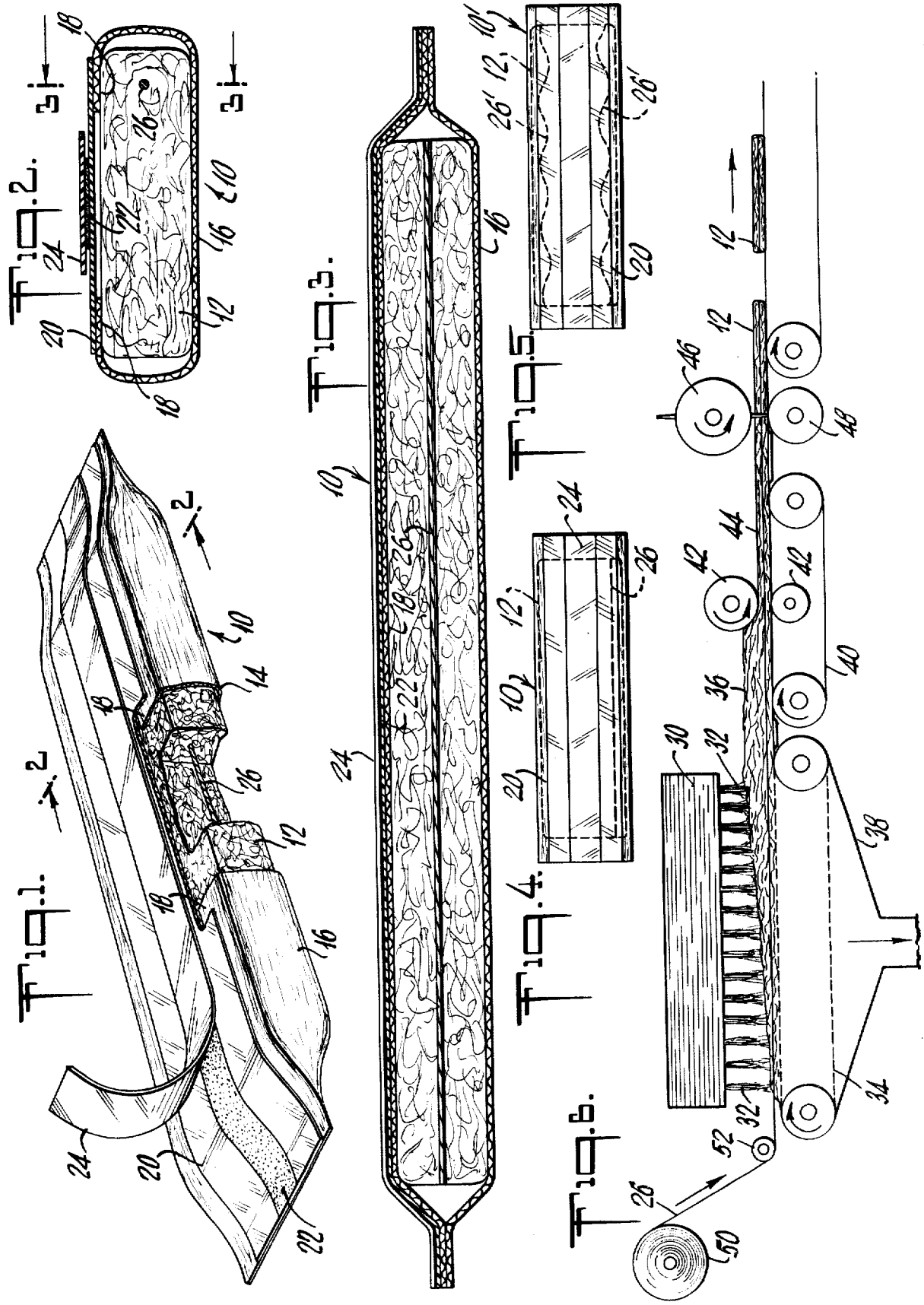

4,237,591

DEODORANT MINI-PAD SANITARY NAPKIN

BACKGROUND OF THE INVENTION

This is a division of my patent application Ser. No. 799,850, filed on May 23, 1977 now abandoned.

This present invention relates to sanitary napkins and more particularly relates to sanitary napkins being provided with perfumes or deodorants for masking or otherwise reducing the perception of malodorous body fluids absorbed and retained by the napkins in use.

Sanitary napkins generally comprise an elongated absorbent body or pad of such absorbent materials as wood pulp, cotton, wadding and the like having two major surfaces, one of which is to be worn against the body of the user and the other away from the body. The surface worn against the body is often provided with a porous cover for containing the absorbent material and this cover may extend completely or partially around the pad. The surface worn away from the body generally has an impervious cover overlying it to preclude body fluids absorbed by the pad from transferring through the pad and onto the undergarment or other clothing of the wearer. This impervious cover can be provided on the outer most surface of the napkin or below the porous cover if such porous cover extends around the entire pad. Recently, the described sanitary napkins have been provided with a layer of pressure sensitive adhesive overlying the outer most surface of the napkin on the surface worn away from the body. The purpose of this pressure sensitive adhesive is to adhere to the crotch portion of the user's undergarment and preclude the napkin from shifting from the intended in-use position.

The above-described napkins are generally worn during menstruation for a period of time up to several hours in the course of which time they absorb and retain a substantial quantity of menstrual fluid. This retained menstrual fluid is known to contain various highly malodorous compounds such as amines and fatty acids. To obviate the potential for embarrassment and discomfort for the user, the art has long sought methods for masking or otherwise deodorizing such products. These prior art suggestions have considered adding, generally to the absorbent pad, deodorizing agents or perfumes in the form of either powders or liquids. In each instance, the addition of either of these two forms of agents has created problems. In the case of powders, it has been difficult to incorporate and maintain such materials into a pad comprised of loosely associated absorbent material. Instead, there is a tendency for the powders to dust out. Further, powders are difficult to handle on the high speed processing equipment used to manufacture sanitary napkins.

Accordingly, the art has found a preference for using liquid perfumes and deodorants in that these are more easily handled in manufacturing procedures. It has been suggested that the absorbent pad of the product be impregnated with perfumes or have a line of perfume extruded onto its surface prior to being incorporated into a sanitary napkin. While the employment of impregnated or extruded liquids has the great advantage of simplifying manufacturing procedures, this method has been discovered to have serious drawbacks, particularly when employed in the manufacture of napkins having, as the impervious cover, a film of polymeric material such as polyethylene and still more particularly when such napkins are further provided with a pressure sensitive adhesive attachment system. It has been discovered that as the products age, e.g., during storage or on the shelf of a retailer, there is a definite tendency for the impregnated or extruded liquid to migrate into the impervious film cover and into the pressure sensitive adhesive. The nature of perfumes generally used is such that migration into the film cover disadvantageously acts to plasticize the cover, rendering it weak or easily torn and, in any event, forming wrinkles which are aesthetically undesirable. Even more disadvantageously, migration of the perfume into the pressure sensitive adhesive, seriously degrades the adhesive to the point where it losses a significant proportion of its cohesive properties, is unsatisfactory in maintaining the napkin in its proper in-use position, and tends to delaminate from the impervious cover and be deposited onto the user's undergarment.

In view of these drawbacks, there is a need to provide a more effective sanitary napkin having a liquid perfume therein and a method for manufacturing such a napkin.

SUMMARY OF THE INVENTION

In accordance with this invention, it has been discovered that a sanitary napkin may be provided having a liquid perfume therein in a manner by which the perfume will be greatly inhibited from undesirably migrating to certain areas of the napkin. In particular, a sanitary napkin is provided comprising an elongated and generally rectangular absorbent body or pad having first and second major surfaces. The first major surface is intended to be worn against the body and the second major surface is intended to be worn away from the body. An impervious cover overlies the second major surface and preferably, there is provided on this impervious cover, a layer of pressure sensitive adhesive for maintaining the napkin in position during use.

The napkin is provided with a perfume composition which generally comprises a formulation of essential oils, solvents and other additives designed to provide the perfume composition with desired properties. In accordance with this invention, means are provided for inhibiting the migration of the perfume composition components to undesired areas of this napkin. These perfume migration inhibiting means comprise providing at least one elongated narrow strip element carrying said perfume, the element extending generally longitudinally within the napkin. Preferably the element is buried within the absorbent body of the napkin. It has been discovered that, for reasons not yet totally understood, by concentrating the perfume composition on the narrow element and preferably burying this element within the absorbent body, the tendency for migration of the components of the perfume toward the impervious cover and the pressure-sensitive adhesive is greatly inhibited and products made in this manner may be stored for long periods of time without the adverse effects on the cover or the adhesive heretofore experienced.

The narrow strip element may take the form of ribbons of woven or nonwoven fabric or filaments of natural or synthetic materials as, for example, strips of cloth, gauze, tissue or the like. The preferred form, however, is a string or yarn of cotton, rayon, polyester or other cellulosic material impregnated with the liquid perfume.

In another aspect of this invention, a method is provided for manufacturing the above-described sanitary napkin. In accordance with this method, a supply of the narrow element material is provided carrying the requisite quantity of perfume. For example, a spool of rayon string that has been impregnated with the liquid perfume is provided. The narrow element is fed into a pad forming device which consists essentially of an endless air-pervious belt onto which loose particles or fibers of absorbent material is air-laid to form a continuous ribbon of loosely associated absorbent material. The narrow element is suspended above and longitudinal with the belt so that the continuous ribbon of absorbent material is formed around the element. The ribbon is then compacted by passing under compression rolls and is covered and cut into individual sanitary napkins.

BRIEF DESCRIPTION OF THE DRAWINGS

The improvements of the present invention will be more readily understood by reference to the following drawings in which:

FIG. 1 is a perspective view of a sanitary napkin of the present invention as viewed onto the major surface intended to be worn away from the body and with parts removed to show internal construction;

FIG. 2 is a transverse, cross-sectional, view of the napkin of FIG. 1 taken through line 2—2 of FIG. 1;

FIG. 3 is a longitudinal cross-sectional view of the napkin of FIG. 2 taken through line 3—3 of FIG. 2;

FIG. 4 is a plan view of the napkin of FIG. 1;

FIG. 5 is a plan view of another embodiment of the invention; and

FIG. 6 is a schematic, longitudinal, cross-sectional view of a manufacturing line for producing the absorbent pads for use in the sanitary napkins of this invention.

DETAILED DESCRIPTION OF THE INVENTION

Referring now to FIGS. 1–4, there is illustrated a sanitary napkin 10 embodying the teachings of the invention. The napkin 10 comprises an absorbent body or pad 12 which can be made from any of the many well-known materials having body fluid absorbing properties such as comminuted wood pulp, cotton linters, rayon fibers, cotton staple, bleached sulfite creped wadding reconstituted cellulose foams, natural sponges, chemically modified cellulose, synthetic absorbent materials such as hydrophilic polyurethane and the like and combinations thereof. When the absorbent material is loosely associated particulate matter, e.g., fibers, powders, crumbs or the like, the absorbent body 12 is provided with a body fluid pervious cover 14 which covers the major surface 16 intended to be worn against the body of the user and may also cover the sides of the absorbent body as well as portions of the major surface 18 intended to be worn away from the body. As shown in the specific embodiment of the drawings, the porous cover 14 can be a knitted, woven, or nonwoven fabric or paper made from a variety of cellulosic, or synthetic materials. It will also be understood that in certain circumstances, as when the absorbent body 12 has sufficient integrity, the need for a porous cover may be obviated and the cover dispensed with. For example, the absorbent body may take the form of molded polyurethane or cellulosic foam or of fiberous absorbent material having an adhesive binder dispersed therein to give the body 12 structural integrity. In these instances, a pervious cover may be unnecessary.

Overlying the surface 18 worn away from the body is a fluid impervious barrier sheet 20 which can be made, for example, of such film forming materials as polyethylene, polyproplylene, cellophane, or from impregnated fluid repellent paper or similar fluid impervious sheet-like materials.

The barrier sheet 20 and the cover 14 may be sealed together to envelop the absorbent body by means well-known in the art such as, for example, by use of adhesives (not shown).

The outer surface of barrier sheet 20 is provided with a layer of pressure sensitive adhesive preferably taking the form of at least one narrow adhesive band 22 which preferably extends throughout the longitudinal direction of the napkin. As described above, the adhesive is provided to adhere the napkin to the crotch portion of the wearer's undergarment and retain the napkin in proper position during use. The adhesive band may comprise any of a large number of pressure sensitive adhesives available on the market, including, for example, the so-called cold pressure sensitive adhesives such as the acrylate adhesives, e.g., vinyl acetate-2 ethyl hexyl acetate copolymer which is generally combined with tackifiers such as, for example, ethylene amine. Alternatively, the adhesive may comprise the rapid setting themoplastic (hot melt) adhesives such as block copolymers exemplified by styrene-isoprene, styrene-ethylenebutylene and butadiene-styrene copolymers. The adhesive band may also comprise a two-sided adhesive tape.

The adhesive band is protected by a releasable strip 24, illustrated in FIG. 1 in a partially peeled off position, and provided to protect the adhesive during storage and handling prior to use.

In accordance with the teachings of the invention, the sanitary napkin 10 is provided with a masking or deodorizing perfume and means are provided for inhibiting the migration of components of the perfume composition to the barrier sheet 20 and the pressure sensitive adhesive band 22. These means comprise providing a carrier for the perfume composition consisting of at least one elongated narrow element extending longitudinally within the napkin. This narrow element is exemplified in the embodiment illustrated in the drawings as a string 26 impregnated with a liquid perfume composition and buried within the absorbent body 12. It will be understood by one skilled in the art that while a string is used to exemplify the invention, various forms of elongated narrow elements may be employed for carrying the perfume. For example, the narrow element may take the form of a narrow ribbon of woven or nonwoven fabric or a thin, narrow strip of film material such as polyethylene, cellophane, or the like.

As hereinafter used, the expression "narrow strip elements" is intended to mean fibrous or film material as yarn, string, tape or ribbon or equivalent, much narrower than the absorbent bodies which are the product of the process described herein.

In some cases, the element must be provided with means for insuring that the perfume is carried on the element, such as adding substances which will cause the perfume to adhere to the element. Preferably, however, the element is in the form of a string or yarn of material which can easily be impregnated with the preferred liquid perfumes as, for example, a length of cellulose (e.g., cotton or rayon) string or yarn. String is characterized by the count of the yarn and the number of plies of yarn that are braided together and is available in a wide range of these parameters. Count is a number indicative of the weight per unit length of the braided string. Generally, a string satisfactory for the purpose of this invention is one which is strong enough to withstand processing and which can carry the requisite quantity of perfume, preferably by being impregnated with the perfume. Suitable strings for this purpose are polyester, rayon and cotton strings having counts from about 2 to about 8 in 2, 3, 4, or 5 plies. These exhibit tensile strengths of at least 10 pounds and yield from about 600 to about 1,950 yards per pound. The string may be impregnated with liquid perfume by unwinding from a spool, drawing the string through a perfume bath and then rewinding the string onto a second spool. Preferably the rewound spool is conditioned by allowing it to age for a period of time in a hermetically sealed bag to allow the perfume to become uniformly distributed on the spool.

The amount of perfume which the string should carry is, of course, primarily a function of the quantity of perfume desired in each napkin. Generally, this value is about 0.02 to 0.08 gm/napkin. Accordingly, for the embodiment shown in FIGS. 1-4, wherein a single straight strand of string is contained within a napkin having a pad length of, for example, six inches, the string should carry about 0.0033 to about 0.0133 gm. of perfume per inch. Naturally, if two straight strands were used in the same napkin, this required carrying capacity of the string would be reduced by a factor of two. In FIG. 5, a sanitary napkin 10' illustrates still another variation in which two strings 26' are employed and extended through the longitudinal length of the napkin pad in a non-linear, wavy pattern. In this instance, for a six-inch pad, still less carrying capacity is required per unit length of string.

The particular perfumes carried by the elongated narrow elements of this invention form no part of this invention and may be varied to so great a degree as to defy classification or description. Reference is instead made herein to "Cosmetics, Science and Technology," second edition, edited by M. S. Balsam and Edward Sagain and published by John Wiley & Sons, inc. of New York, 1972. In particular, reference is made to Chapter 32 "Fragrance," written by M. S. Balsam for examples of the variety of perfume formulations possible.

Referring now to FIG. 6, illustrated therein, in schematic cross-sectional view, is one method of incorporating the elongated narrow element into the absorbent body or pad 12 of the sanitary napkin of this invention. A source of supply 30 of loosely associated absorbent material 32 is laid down onto an endless, air pervious, moving belt 34 on which is progressively built up a loosely associated ribbon 36 of the absorbent material. To facilitate the forming of this ribbon 36, air is aspirated from beneath the belt in the direction shown by the arrow in the drawing, the aspiration being made effective by enclosing the volume below the belt 34 in a housing 38. The means for aspirating (not shown) may be, for example, a common air-vacuum pump. The loosely associated ribbon 36 passes from the air-pervious endless belt 34 onto a second endless belt 40 and between the nip of compression rollers 42 wherein it is formed into a densified absorbent ribbon 44. After passing compression roller 42, the densified ribbon is then passed to rotating knife 46 which cooperates with an anvil roller 48 to cut the densified ribbon into the desired lengths of absorbent bodies 12 for use in the sanitary napkins of this invention.

A supply spool 50 of the elongated narrow element which carries the perfume, i.e., string 26, is unwound, and is passed under guide roller 52 and suspended over and longitudinal with air-pervious endless belt 34. The string 26 is then gripped and pulled through compression rollers 42. As can be seen from the drawings, the loosely associated ribbon 36 is formed around the suspended string 26 which remains within the ribbon as it is compressed by the compression rollers 42 and passed to the knife 46. The knife then cuts not only the densified ribbon 44 but likewise the string 26 into lengths desired for use in the napkins of this invention.

COMPARATIVE EXAMPLE

A series of sanitary napkin samples were prepared to investigate the migration of components of a perfume placed within each napkin by various methods and also by the method in accordance with the teachings of this invention. Each of the sanitary napkins used conformed in size, weight and construction to the unscented, adhesively attached, sanitary napkin now being sold by Personal Products Company of Milltown, New Jersey, as STAYFREE Mini-Pads. Such napkins have the configuration shown in FIG. 1 of the drawings and comprise a pad of wood-pulp fluff measuring approximately $6\frac{1}{4} \times 1\frac{5}{8} \times \frac{1}{4}$ inches and weighting about 3 gms. The napkins are provided with a porous nonwoven cover and a polyethylene barrier sheet approximately 2 mils thick. The pressure sensitive adhesive used is of the hot melt variety and comprises styrene/isoprene copolymer.

The napkins were equally divided into Sample sets and each napkin was provided with 0.04 gms. of a liquid perfume composition comprising essential oils and diethyl phthalate as a diluent. The placement of the perfume was as follows:

Sample 1—A line of perfume composition was extruded onto the pulp pad directly below the polyethylene barrier film and the pressure sensitive adhesive.

Sample 2—A line of perfume composition was extruded onto the pulp pad directly below the polyethylene barrier film and adjacent a longitudinal edge of the napkin.

Sample 3—A line of perfume composition was extruded onto the body-contacting surface of the pulp pad and in the longitudinal center of this surface.

Sample 4—A line of perfume composition was extruded onto a longitudinal side of the pulp pad near the body-contacting surface.

Sample 5—A two-ply, two-count, bleached white, absorbent, rayon string yielding about 890 yds./lb. was impregnated with the perfume composition and placed into the approximate center of the pad using the method described herein to produce the configuration shown in FIG. 1.

Each set of samples was stored for several weeks at ambient conditions in paper-board boxes with forty-eight napkins to a box. From time to time, samples were removed and tested for the presence of diethyl phthalate in the pressure sensitive adhesive. The analytical method used for this was attenuated total reflectance infrared spectroscopy, as is described in "Internal Reflection Spectroscopy", N. J. Harrick, John Wily & Sons, N.Y. 1967. The equipment used was a Perkin Elmer 621 Infrared Spectrophotometer provided with a Harrick variable angle ATR accessory. A thallium iodide-thallium bromide crystal, designated as KRS-S SPT, measuring 52×20×2 mm, cut at an angle of 45° and having 25 internal reflections, is employed. The crystal was covered on both sides with the sample and the angle of incidence is adjusted to 50°. The presence of phthalate was qualitatively detected by an absorption band at 1280 cm$^{-1}$.

The samples were examined for the presence of phthalate migration and the condition of the polyethylene film. The results of this examination is summarized in Table I.

TABLE I

SUMMARY OF SCENTED MINI-PAD AGING STUDY

| Sample | Perfume Placement | Result |
|---|---|---|
| 1 | Extruded Between Pulp and Barrier Film Under Adhesive Line | Migration into Adhesive Within 1 Week<br>Barrier Film Wrinkling<br>Migration onto Adjacent Napkin |
| 2 | Extruded Between Pulp and Barrier Film Near Edge of Film | Migration into Adhesive Within 3 Weeks<br>Barrier Film Wrinkling<br>Migration onto Adjacent Napkin |
| 3 | Extruded on Pulp in Center of Body-Contacting Surface | Slight Migration into Adhesive Within 8 Weeks<br>No Barrier Film Wrinkling<br>Migration onto Adjacent Napkin |
| 4 | Extruded on Longitudinal Side of Pulp | Slight Migration into Adhesive Within 8 Weeks<br>No Barrier Film Wrinkling<br>Migration onto Adjacent Napkin |
| 5 | Incorporated onto a String Placed in Center of Pulp Pad | Slight Migration into Adhesive Within 8 Weeks<br>No Barrier Film Wrinkling<br>No Migration onto Adjacent Napkin |

As can be seen from Table I, it is only Sample 5 embodying the teachings of this invention which exhibits inhibition of migration into the adhesive, no barrier film wrinkling and no migration onto the adjacent napkins.

What is claimed is:

1. A process for manufacturing elongated absorbent bodies having a perfume composition disposed therein comprising:
   providing a supply of elongated narrow strip elements carrying said perfume composition;
   continuously feeding said narrow elements into a pad-forming device comprising an endless air-pervious belt and means for air-laying loose particles of absorbent material thereon;
   suspending said strip elements above and longitudinal with said belt; and
   air-laying loose particles of absorbent material onto said belt and around at least one of said strip elements to form an absorbent body having at least one of said perfume composition carrying strip elements disposed therein said narrow strip element providing the only perfume in said body.

2. The process of claim 1 wherein said strip elements are impregnated to 0.2 to about 0.08 grams of perfume composition per absorbent body.

3. The process of claim 1 wherein said strip elements are ribbons of woven fabric.

4. The process of claim 1 wherein said strip elements are ribbons of non-woven fabric.

5. The process of claim 1 wherein said strip elements are cellulosic.

6. The process of claim 1 wherein said strip elements are strings.

7. The process of claim 1 wherein said strip elements are strings impregnated with a perfume composition, said strings being continuous and having been unwound from a spool, drawn through a perfume bath, and then rewound onto a second spool prior to being fed into said pad forming device.

8. The process of claim 7 wherein said rewound string is conditioned by aging for a period of time in a hermitically sealed bag whereby said perfume becomes uniformly distributed on said rewound string.

* * * * *